(12) United States Patent
Jackson et al.

(10) Patent No.: US 8,728,512 B2
(45) Date of Patent: May 20, 2014

(54) TREATMENT AND COMPOSITION FOR WOUND HEALING

(75) Inventors: Christopher John Jackson, Mt. Colah (AU); Philip Neil Sambrook, Centennial Park (AU)

(73) Assignee: Christopher John Jackson, New South Wales (AU)

( * ) Notice: Subject to any disclaimer, the term of this patent is extended or adjusted under 35 U.S.C. 154(b) by 0 days.

(21) Appl. No.: 12/504,898

(22) Filed: Jul. 17, 2009

(65) Prior Publication Data
US 2013/0280234 A1 Oct. 24, 2013

Related U.S. Application Data

(63) Continuation of application No. 10/480,586, filed as application No. PCT/AU02/00751 on Jun. 11, 2002, now abandoned.

(30) Foreign Application Priority Data

Jun. 13, 2001 (AU) .......................................... 5637
Apr. 2, 2002 (AU) .......................................... 1433

(51) Int. Cl.
*A61F 13/00* (2006.01)
*A61K 9/70* (2006.01)

(52) U.S. Cl.
USPC ........................................................ 424/443

(58) Field of Classification Search
USPC ........................................................ 424/443
See application file for complete search history.

(56) References Cited

U.S. PATENT DOCUMENTS

| | | | |
|---|---|---|---|
| 5,279,956 A | 1/1994 | Griffin et al. | |
| 5,571,786 A | 11/1996 | Eibl et al. | |
| 5,583,102 A | 12/1996 | Lentz et al. | |
| 5,648,380 A | 7/1997 | Martin | |
| 6,008,199 A | 12/1999 | Grinnell et al. | |
| 6,174,855 B1 | 1/2001 | Hansson | |
| 6,197,325 B1 | 3/2001 | MacPhee et al. | |
| 6,200,587 B1 | 3/2001 | Soe et al. | |
| 2003/0073632 A1* | 4/2003 | Ciaccia et al. ................... | 514/12 |

FOREIGN PATENT DOCUMENTS

| | | | |
|---|---|---|---|
| CA | 2068630 C | 4/2003 | |
| JP | 08325161 A | 12/1996 | |
| WO | 9402172 A1 | 2/1994 | |
| WO | 9530429 A1 | 11/1995 | |
| WO | WO 99/20293 | * 10/1998 | |
| WO | 9920293 A1 | 4/1999 | |
| WO | WO 95/30429 | * 5/1999 | |
| WO | 0037022 A2 | 6/2000 | |
| WO | 0156532 A3 | 8/2001 | |
| WO | 0172328 A2 | 10/2001 | |

OTHER PUBLICATIONS

Hirose et. al. (Annals of Surgery (2000) 232:272-280).*
Orimo et. al. (The Journal of Dermatology (2001) 28:511-513).*
Braddock et. al. (International Journal of Dermatology (1999)38:808-817).*
Hirose, Koji, et al., "Activated Protein C Reduces the Ichemia/Reperfusion-Induced Spinal Cord Injury in Rats by Inhibiting Neutrophil Activation," Annals of Surgery, 232(2): 272-280 (2000).
Taoka, Yuji, et al., "Activated Protein C Reduces the Severity of Compression-Induced Spinal Cord Injury in Rats by Inhibiting Activation of Leukocytes," The Journal of Neuroscience, 18(4): 1393-1398 (Feb. 15, 1998).
Nguyen, Minh, "Activated Protein C Directly Activates Human Endothelial Gelatinase A," The Journal of Biological Chemistry, 275(13): 9095-9098 (Mar. 31, 2000).
Okada, Akiko, et al., "Expression of Matrix Metalloproteinases during Rat Skin Wound Healing: Evidence that Membrane Type-1 Matrix Metalloproteinase is a Stromal Activator of Pro-Gelatinase A," The Journal of Cell Biology, 137(1): 67-77 (Apr. 7, 1997).
Okajima, Kenji et al., "Protein C as a New Treatment Drug," Clinical Hematology, 33(6): 767-769 (1992) with English language abstract.
Matsubara, Masao, "Corneal Wound Healing and Collagen, Matrix Metalloproteinase and Its Inhibitors," Clinical Ophthalmology, 51(11): 215-217 (extra edition) (1997) with English language abstract.
Tsuboi, Ryoji, "Wound Healing and Neovascularization," Experimental Medicine, 9(2): 41-46 (1991) with English language abstract.
Bello, Ysabel, et al., "Recent Advances in Wound Healing," JAMA, Feb. 9, 2000, pp. 716-718, vol. 283(6). American Medical Association.
Braddock, Martin et al., "Current therapies for wound healing; electrical stimulation, biological therapeutics, and the potential for gene therapy," International Journal of Dermatolgoy, Nov. 1999, pp. 808-817, vol. 38(11). Blackwell Science Ltd.
Esmon, Charles T., "The Anticoagulant and Anti-Inflammatory Roles of the Protein C Anticoagulant Pathway," Journal of Autoimmunity, 2000, pp. 113-116, vol. 15. Academic Press.
Inkinen, Kaija et al., "Expression and activity of matrix metalloproteinase-2 and -9 in experimental granulation tissue," APMIS, May 2000, pp. 318-328, vol. 108(5). Munksgaard International Publishers Ltd.
Orimo, Hiroshi et al., Letters to the Editor, "A Leg Ulcer Due to Protein C Deficiency: Successful Treatment with Split Thickness Skin Graft after Protein C Supplementation," The Journal of Dermatology, 2001, pp. 511-513, vol. 28.
Singer, Adam J. et al., "Mechanisms of Disease: Cutaneous Wound Healing," The New England Journal of Medicine, Sep. 2, 1999, pp. 738-746, vol. 341(10). Massachachusetts Medical Society.

* cited by examiner

*Primary Examiner* — Marcos Sznaidman
(74) *Attorney, Agent, or Firm* — Myers Bigel Sibley & Sajovec, P.A.

(57) ABSTRACT

A method and medicament for promoting wound healing in a subject is disclosed. The medicament comprises an effective amount of an agent comprising one or more of;
  (i) an activated protein C (APC),
  (ii) a functional fragment of an APC,
  (iii) an APC mimetic compound, and
  (iv) protein C.
Delivery systems including gels, sponges, gauzes and meshes incorporating the agent for topical administration are also described.

11 Claims, 6 Drawing Sheets

TREATMENT AND COMPOSITION FOR WOUND HEALING

CROSS-REFERENCE TO RELATED APPLICATIONS

Figure 1:
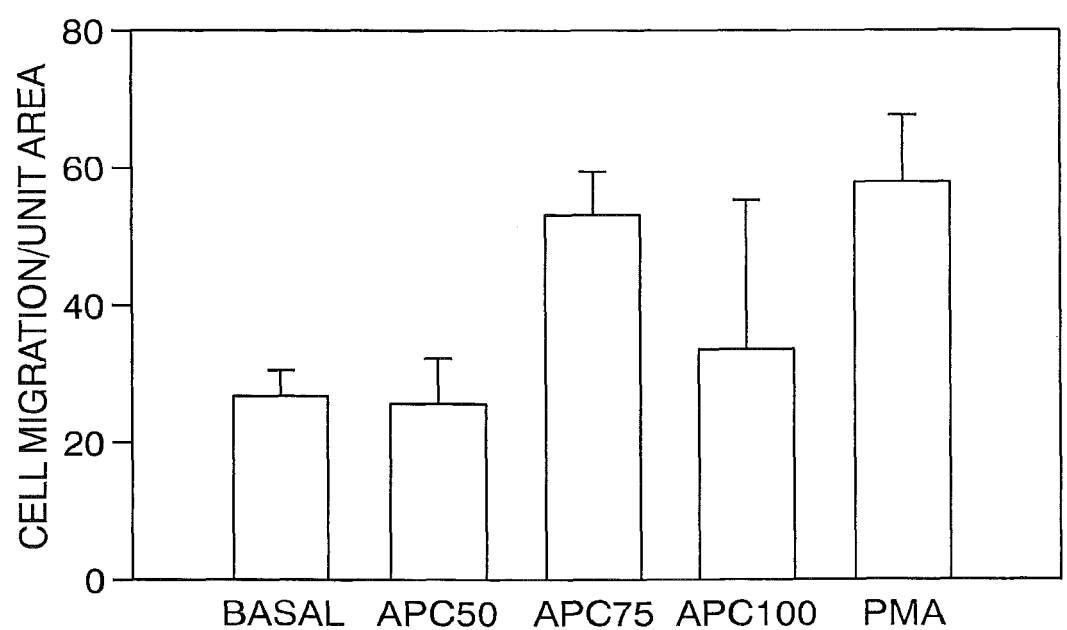

This application is a continuation of U.S. Ser. No. 10/480,586, filed Apr. 30, 2004, which is a filing under 35 U.S.C. 371 of PCT/AU02/00751, filed Jun. 11, 2002, which claimed priority from Australian Patent Application PR 5637, filed Jun. 13, 2001, and Australian Patent Application PS 1433, filed Apr. 2, 2002. These prior applications are incorporated herein by reference.

FIELD OF THE INVENTION

The present invention relates to the field of medicine and, more particularly, to wound healing and methods and compositions for promoting wound healing. In a particular application of the present invention, activated protein C (APC) is administered to a slow healing wound by, for example, topical application.

BACKGROUND TO THE INVENTION

Wounds are internal or external bodily injuries or lesions caused by physical means, such as mechanical, chemical, viral, bacterial, or thermal means, which disrupt the normal continuity of structures. Such bodily injuries include contusions, wounds in which the skin is unbroken, incisions, wounds in which the skin is broken by a cutting instrument, lacerations, and wounds in which the skin is broken by a dull or blunt instrument. Wounds may be caused by accidents or by surgical procedures.

The healing of wounds is a complex process involving a number of stages. These include; 1) coagulation, which begins immediately after injury; 2) inflammation, which begins a few minutes later; 3) a migratory and proliferative process (granulation stage), which begins within hours to days; and 4) a remodelling process with subsequent development of full strength skin (1-3).

Coagulation and Inflammation

Coagulation controls haemostasis and initiates healing by releasing a variety of growth factors and cytokines from degranulated platelets. During the inflammation phase, platelet aggregation and clotting form a matrix which traps plasma proteins and blood cells to induce the influx of various types of cells. Neutrophils are the first cells to arrive and function to phagocytise contaminating bacteria, digest the fibrin clot and release mediators to attract macrophages and activate fibroblasts and keratinocytes (3). Macrophages digest pathogens, debride the wound and secrete cytokines/growth factors (eg interleukin-1 (IL-1), epidermal growth factor (EGF), vascular endothelial growth factor (VEGF), transforming growth factor-$\beta$ (TGF-$\beta$), and basic fibroblast growth factor (bFGF)) that stimulate fibroblasts and endothelial cells. Overall, the inflammatory stage is important to guard against infection and promote the migratory and proliferative stages of wound healing.

Granulation and Remodelling of the Extracellular Matrix

These stages include cellular migration and proliferation. Although lymphocytes and macrophages are involved, the predominant cell types are epithelial, fibroblast and endothelial. Within hours of an injury, an epidermal covering, comprised mainly of keratinocytes, begins to migrate and cover the epidermis, a process known as re-epithelialisation. When they completely cover the wound they differentiate and stratify to form a new epidermis with a basal lamina. Angiogenesis (ie the formation of new blood vessels) occurs during this stage and provides nutrients for the developing tissue to survive. Fibroblasts migrate into the wound site and produce collagen and proteoglycans which ultimately give the wound tensile strength. As the remodelling phase progresses, granulation tissue is replaced by a network of collagen and elastin fibers leading to the formation of scar tissue.

Failed Wound Healing

Impaired dermal wound healing and/or dermal ulcers occur in patients with peripheral arterial occlusive disease, deep vein thrombosis, diabetes, pressure sores and burns (4). Despite intense investigation, the molecular mechanisms associated with impaired wound healing are poorly understood.

Wound healing is affected by numerous factors, including local factors (eg growth factors, edema, ischemia, infection, arterial insufficiency, venous insufficiency or neuropathy), systemic factors (eg inadequate perfusion and metabolic disease) and other miscellaneous factors, such as nutritional state, exposure to radiation therapy and smoking.

Leucocytes, particularly neutrophils, and macrophages persist in the surrounding tissue and secrete a range of proteases, including matrix metalloproteinases (MMPs) and serine proteases (5). Excessive accumulation of these enzymes interferes with the matrix remodelling (6). It is thought that agents which inhibit proteases will benefit wound healing (7). Another feature of some chronic wounds is the reduction or absence of angiogenesis, which prevents nutrients from accessing the newly formed tissue (8).

Existing Technologies to Improve Wound Healing

Chronic wounds are initially managed by treatment comprising eschar debridement, antibiotic treatment where appropriate, and regular dressing (2). Other dressings, such as hydrogels, hydrocolloids, or alginates, may also be used. Venous ulceration is treated by compression therapy, whereas arterial or diabetic ulcers require regular changes of dressings. Pressure sores are encouraged to heal by the relief of pressure at the injury site. Some other physical devices such as laser treatment, hyperbaric oxygen and electrical stimulation for arterial ulcers, are also used to promote wound healing (2, 9, 10).

For wounds that are unresponsive to such interventions, the use of tissue-engineered skin, such as Dermagraft or Apligraf, is an option. This therapy acts to prevent bacterial infection and allows the wound the chance to heal by normal reparative processes (11, 12). The use of such skin replacements to accelerate wound healing depends on the availability of an existing vascular supply in the existing wound.

Another approach to wound healing involves the administration of growth factors/cytokines, which have been shown to accelerate cell proliferation in vitro and/or to promote wound healing in some animal models. These include IL-1, platelet-derived growth factor (PDGF), EGF, VEGF, TGF-$\beta$, and bFGF (2). Procuren (Curative Technologies), an autologous platelet releasate, contains at least five growth factors, that aid in the formation of granulation tissue and re-epithelialisation. This autologous growth factor mix has achieved some success in human subjects with ulcerated limb lesions (13). However, on the whole, results from most clinical trials using growth factors/cytokines have been disappointing. For example, EGF failed to heal venous stasis ulcers and IL-1 failed to treat pressure sores effectively (2). Similar results were reported using bFGF (14). The reason for the lack of efficacy is not certain, but may relate to the multifactorial effects, some undesirable for healing, of growth factors/cytokines.

Thus, there is an ongoing need to identify and develop new agents for the promotion of wound healing.

Activated protein C (APC) is a serine protease having a molecular weight of about 56 kD that plays a central role in physiological anticoagulation. The inactive precursor, protein C, is a vitamin K-dependent glycoprotein synthesised by the liver and endothelium and is found in plasma. Activation of protein C occurs on the endothelial cell surface and is triggered by a complex formed between thrombin and thrombomodulin (15, 16). Another endothelial specific membrane protein, endothelial protein C receptor (EPCR), has been shown to accelerate this reaction more than 1000-fold (17). Endothelial APC functions as an anticoagulant by binding to the co-factor, protein S, on the endothelial surface, which inactivates the clotting factors Factor VIIIa and Factor Va. The importance of APC as an anticoagulant is reflected by the findings that deficiencies in this molecule result in familial disorders of thrombosis (18).

Recently, it has also been reported that APC additionally acts as an anti-inflammatory agent and directly activates the protease, gelatinase A (17, 20). Gelatinase A is secreted by many different cell types, including smooth muscle cells, fibroblasts and endothelial cells. By degrading the collagens present in the basement membrane (21) and allowing cells to invade the stroma, gelatinase A plays an important role in physiological remodelling and angiogenesis (22). Gelatinase A also plays an important role in numerous diseases, such as promoting the invasion of thymic epithelial tumors (23), promoting the destruction of the joint in arthritis by cleaving collagen from the cartilage matrix (24) and contributing to cardiac mechanical dysfunction during reperfusion after ischemia (25). In addition to its ability to degrade the matrix, gelatinase A can also target other substrates. For example, it cleaves big endothelin-1 to yield a potent vasoconstrictor, implicating gelatinase A as a regulator of vascular reactivity (26). Gelatinase A release can also mediate platelet aggregation (27).

Further, and as is demonstrated in the examples provided hereinafter, APC is also able to promote regeneration of endothelial cells after wounding in vitro, stimulate re-epithelialisation, fibroblast invasion and angiogenesis in a chicken embryo and enhance wound healing in a rat wounding model. These functions when taken together with the abovementioned anticoagulating, anti-inflammatory and Gelatinase A-activating functions, strongly indicate that APC, functional fragments thereof, and the precursor of APC (ie protein C) is/are useful for the treatment of wounds and, particularly, slow-healing wounds.

SUMMARY OF THE INVENTION

Thus, in a first aspect, the present invention provides a method for promoting wound healing in a subject, said method comprising administering to said subject an effective amount of an agent comprising one or more of;
(i) an APC,
(ii) a functional fragment of an APC,
(iii) an APC mimetic compound, and
(iv) protein C,
optionally in admixture with a pharmaceutically-acceptable carrier.

In a second aspect, the present invention provides a medicament for promoting wound healing in a subject, said medicament comprising an amount of an agent comprising one or more of;
(i) an APC,
(ii) a functional fragment of an APC,
(iii) an APC mimetic compound, and
(iv) protein C,
in admixture with a pharmaceutically-acceptable carrier.

In a third aspect, the present invention provides a delivery system (eg a gel, sponge, gauze or mesh) incorporating an amount of an agent comprising one or more of;
(i) an APC,
(ii) a functional fragment of an APC,
(iii) an APC mimetic compound, and
(iv) protein C,
said delivery system being suitable for application to a wound and thereafter promoting wound healing.

In a fourth aspect, the present invention provides the use of an agent comprising one or more of;
(i) an APC,
(ii) a functional fragment of an APC,
(iii) an APC mimetic compound, and
(iv) protein C,
for the preparation of a medicament for promoting wound healing in a subject.

In a fifth aspect, the present invention provides the use of an agent comprising one or more of;
(i) an APC,
(ii) a functional fragment of an APC,
(iii) an APC mimetic compound, and
(iv) protein C,
for the preparation of a delivery system, said delivery system being suitable for application to a wound and thereafter promoting wound healing.

DETAILED DISCLOSURE OF THE INVENTION

The APC and/or protein C utilised in the present invention may be obtained by purification from a suitable source (eg blood taken from humans or other animals) or produced by standard recombinant DNA techniques such as is described in, for example, Maniatis, T. et al., Molecular Cloning: a laboratory manual, Second Edition, Cold Spring Harbor Laboratory Press. Recombinant APC or protein C may incorporate modifications (eg amino acid substitutions, deletions, and additions of heterologous amino acid sequences), which may, for example, enhance biological activity or expression of the respective protein. However, preferably, the present invention utilises human APC and/or protein C. The APC and/or protein C may also be glycosylated by methods well known in the art and which may comprise enzymatic and non-enzymatic means.

Suitable functional fragments of an APC may be produced by cleaving purified natural APC or recombinant APC with well known proteases such as trypsin and the like, or more preferably, by recombinant DNA techniques or peptide/polypeptide synthesis. Such functional fragments may be identified by generating candidate fragments and assessing biological activity by, for example, assaying for activation of MMP-2, promotion of repair of a wounded endothelial monolayer and/or angiogenesis in chicken embryo chorio-alantoic membrane (CAM) in a manner similar to that described in the examples provided herein. Preferably, functional fragments will be of 5 to 100 amino acids in length, more preferably, of 10 to 30 amino acids in length. The functional fragments may be linear or circularised and may include modifications of the amino acid sequence of the native APC sequence from whence they are derived (eg amino acid substitutions, deletions, and additions of heterologous amino acid sequences). The functional fragments may also be glycosylated by methods well known in the art and which may comprise enzymatic and non-enzymatic means.

Suitable APC mimetic compounds (ie compounds which mimic the function of APC) may be designed using any of the methods well known in the art for designing mimetics of peptides based upon peptide sequences in the absence of secondary and tertiary structural information (28). For example, peptide mimetic compounds may be produced by modifying amino acid side chains to increase the hydrophobicity of defined regions of the peptide (eg substituting hydrogens with methyl groups on aromatic residues of the peptides), substituting amino acid side chains with non-amino acid side chains (eg substituting aromatic residues of the peptides with other aryl groups), and substituting amino- and/or carboxy-termini with various substituents (eg substituting aliphatic groups to increase hydrophobicity). Alternatively, the mimetic compounds may be so-called peptoids (ie non-peptides) which include modification of the peptide backbone (ie by introducing amide bond surrogates by, for example, replacing the nitrogen atoms in the backbone with carbon atoms), or include N-substituted glycine residues, one or more D-amino acids (in place of L-amino acid(s)) and/or one or more α-amino acids (in place of β-amino acids or γ-amino acids). Further mimetic compound alternatives include "retro-inverso peptides" where the peptide bonds are reversed and D-amino acids assembled in reverse order to the order of the L-amino acids in the peptide sequence upon which they are based, and other non-peptide frameworks such as steroids, saccharides, benzazepine1,3,4-trisubstituted pyrrolidinone, pyridones and pyridopyrazines. Suitable mimetic compounds may also be designed/identified by structural modelling/determination, by screening of natural products, the production of phage display libraries (29), minimised proteins (30), SELEX (Aptamer) selection (31), combinatorial libraries and focussed combinatorial libraries, virtual screening/database searching (32), and rational drug design techniques well known in the art (33).

The present invention is suitable for promoting wound healing generally, but is particularly suitable for application to the promotion of slow-healing wounds, otherwise known as "chronic wounds", "impaired-healing wounds" or "ulcers", and may be of any of the wound types discussed above. However, preferably, the present invention is applied to wounds selected from the group consisting of;
(i) dermal ulcers such as those associated with pressure, vasculitis, arterial and venous diseases (eg in patients suffering from diabetes, in aged patients, associated with venous insufficiency and cerebrovascular incidents, and resulting from pressure sores or localised areas of tissue damage resulting from direct pressure on the skin or from shearing forces and friction),
(ii) burns,
(iii) oral wounds (eg caused by gingivitis),
(iv) eye wounds (eg corneal wounds resulting from injury, surgery or laser therapy),
(v) non-cutaneous wounds (eg stomach/oesophageal ulcers, vaginal ulcers and internal injury or surgery (including plastic surgery),
(vi) ischemia-reperfusion injury (eg resulting from myocardial infarction),
(vii) bone and cartilage damage as occurs in musculoskeletal disorders such as rheumatoid arthritis and osteoarthritis, and
(viii) warfarin-related skin necrosis.

The agent may be one or a mixture of any or all of the group consisting of an APC, a functional fragment of an APC, an APC mimetic compound, and a protein C.

The agent is preferably administered to a subject after a sufficient period of time since wounding has elapsed such that the coagulation/inflammation stages of the wound healing process have substantially concluded. In practice, it is preferable that administration of the agent occur within 1 to 48 hours after wounding, more preferably within 1 to 10 hours after wounding.

The agent may be administered to a subject through oral or systemic routes or by direct application (e.g. topical administration) to the wound as a medicament formulation, or as incorporated into a delivery system (eg gelatin sponge such as Gelfoam, fine gauze, nylon mesh, or an adhesive plastic strips such as a Band-aid™) which is applied to the wound.

The effective amount of the agent may be expected to vary depending upon the type, site and seriousness of the wound to be treated. It would be well within the skill of persons skilled in the art to adjust the amount appropriately to obtain optimal results. It is, however, expected that generally the effective amount of the agent will be in the range of 0.01 to 10000 μg per kg of body weight, more preferably between 0.1 and 1000 μg per kg of body weight, and most preferably between about 1 and 200 μg per kg of body weight.

Medicaments according to the present invention preferably include an amount of the agent in the range of 0.01 to 1000 μg per g of medicament, in admixture with a pharmaceutically-acceptable carrier (eg gelatin and/or collagen for cream or gel medicaments; isotonic saline, a phosphate buffered solution or the like for drops; or materials such as starch, gelatin, agar, sugar, carboxymethylcellulose, polyvinylalcohol, magnesium stearate, and sodium alginate for dry powders). For use with non-cutaneous wounds and ischemia-reperfusion injury, the medicaments of the present invention may be formulated for oral or systemic administration.

Medicaments and delivery systems (ie gels, sponges, gauzes and meshes) according to the present invention, may contain one or more other active compounds or substances such as other molecules involved in the protein C pathway (eg protein S, EPCR, factor V/Va or factor VIII/VIIIa); antimicrobial agents such as chlorhexidine, povidine-iodine and ciprofloxacin; anticoagulants such as heparin or antithrombin III; steroids such as dexamethasone; inhibitors of inflammation; cardiovascular drugs such as calcium channel blockers; cytokines/growth factors such as epidermal growth factor; local anaesthetics such as bupivacaine; antitumor drugs such as taxol; polyclonal, monoclonal or chimeric antibodies, or functional derivatives or fragments thereof such as antibodies to regulate cell proliferation.

Further, where the medicaments and delivery systems according to the present invention utilise protein C, the medicaments and delivery systems may also include a suitable amount of an agent for activating the protein C (eg thrombin, kallikrein and/or thrombomodulin).

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

The invention will hereinafter be further described by way of the following non-limiting examples and accompanying figures.

BRIEF DESCRIPTION OF ACCOMPANYING FIGURES

FIG. 1 shows the effect of APC on repair of a "wounded" foreskin endothelial (FSE) cell monolayer in culture. Cell monolayers were scraped with a pipette tip, washed and covered with medium containing various amounts of APC, PMA or no treatment. The cells were incubated at 37 degrees C. for 24 hr before being measured for wound closure as described in the example. Results shown represent the number of cells migrating into the wound (mean±SD) per selected unit of area of duplicate wounds. Similar results were obtained in two separate experiments.

Figure 2:
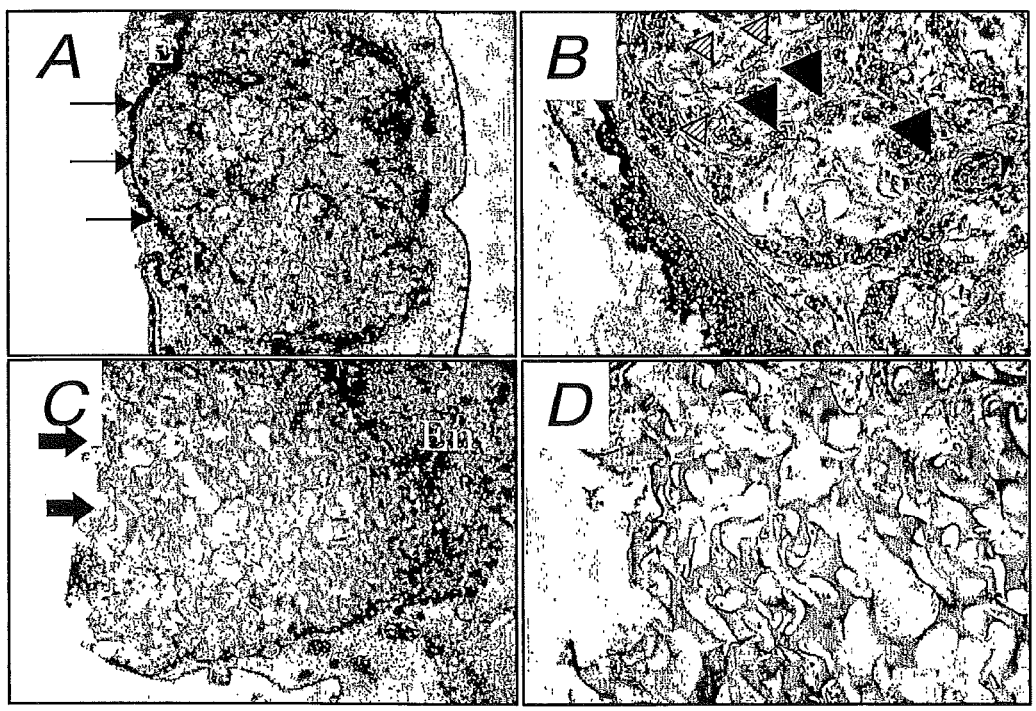

FIG. 2 shows the effect of APC on chicken embryo chorio-allantoic membrane (CAM). Chicken embryos were cracked into a sterile weigh boat on day 1. On day 4, gelatin sponges were treated with 5 μg APC in phosphate buffered saline (PBS) or PBS alone and then placed on top of the CAM. On day 9, the embryos were fixed in Bouin's fluid, sectioned perpendicular to the top surface of the CAM, stained with Masson's stain and viewed under light microscopy. APC-treated CAM showing complete re-epithelialisation over sponge (thin arrows) (A) and many new blood vessels (thick arrows) and fibroblast infiltration (hatched arrows) (B). In the PBS-treated sponges there is no epithelial regrowth (thick arrows) and negligible invasion of cells into the sponge (C,D).

Figure 3:
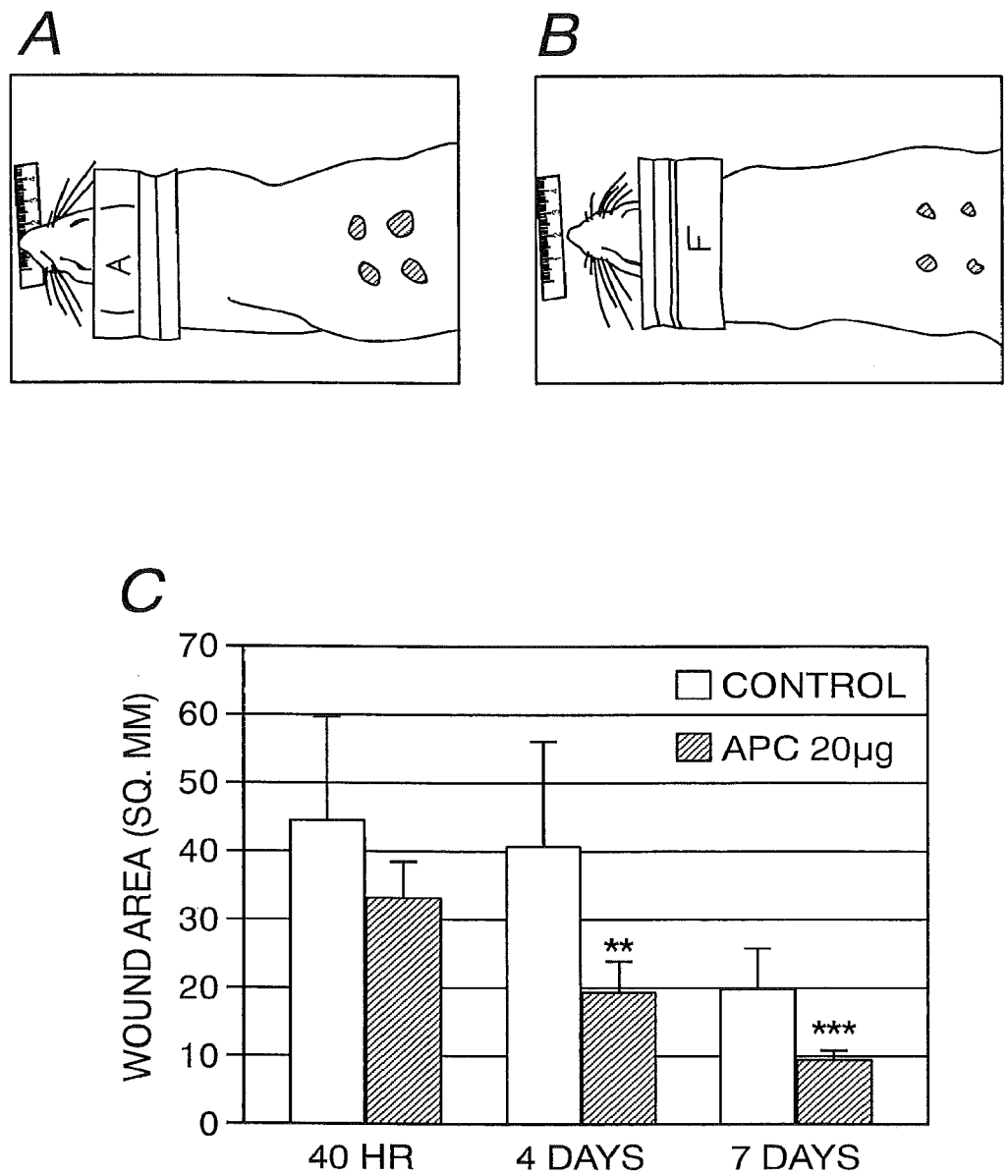

FIG. 3 shows the effect of APC on a rat wound healing model. Sprague-Dawley rats were wounded and then treated with A) saline or B) 20 μg APC and photographed after 4 days. C) Summary of results using 2 rats (total 8 wounds) each treated with saline or 20 μg APC. Results shown are mean+/−S.D of wound area (mm$^2$) after 40 hr, 4 days and 7 days.

Figure 4:
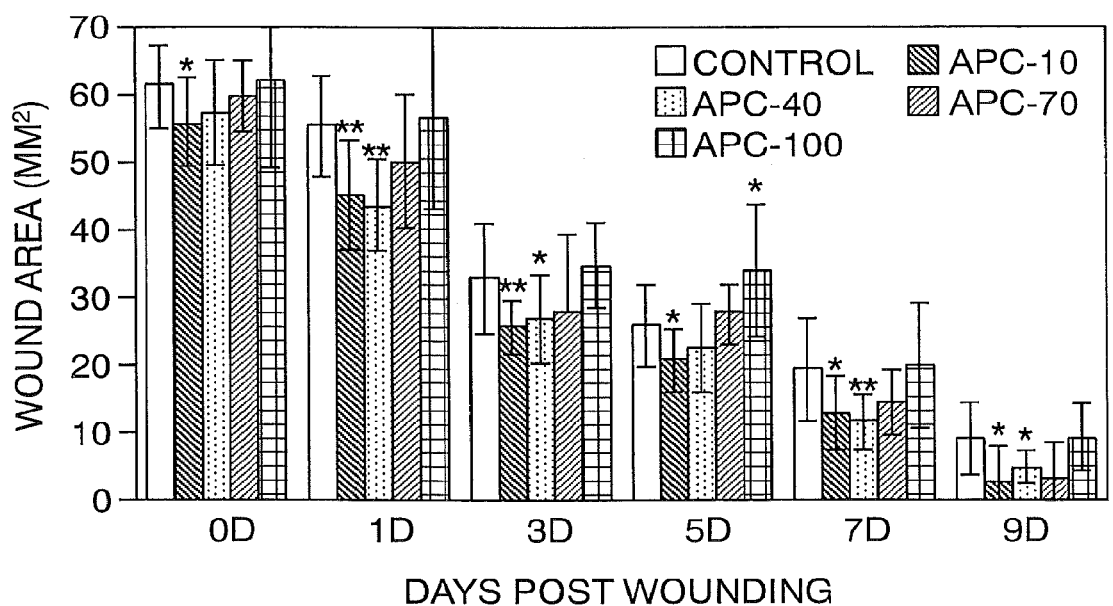

FIG. 4 shows the effect of different doses APC on a rat wound healing model. Normal rats were wounded using an 8 mm punch biopsy and immediately treated with 0 μg (Control, 3 rats, 12 wounds), 10 μg (3 rats, 12 wounds), 40 μg (4 rats, 16 wounds), 70 μg (3 rats, 12 wounds) or 100 μg (3 rats, 12 wounds) of APC. Wound size was measured by image analysis after 1, 3, 5, 7 and 9 days and results shown are mean+/−S.D of wound area (mm$^2$) after 1, 2, 3, 4, 5, 7 and 9 days.

Figure 5:
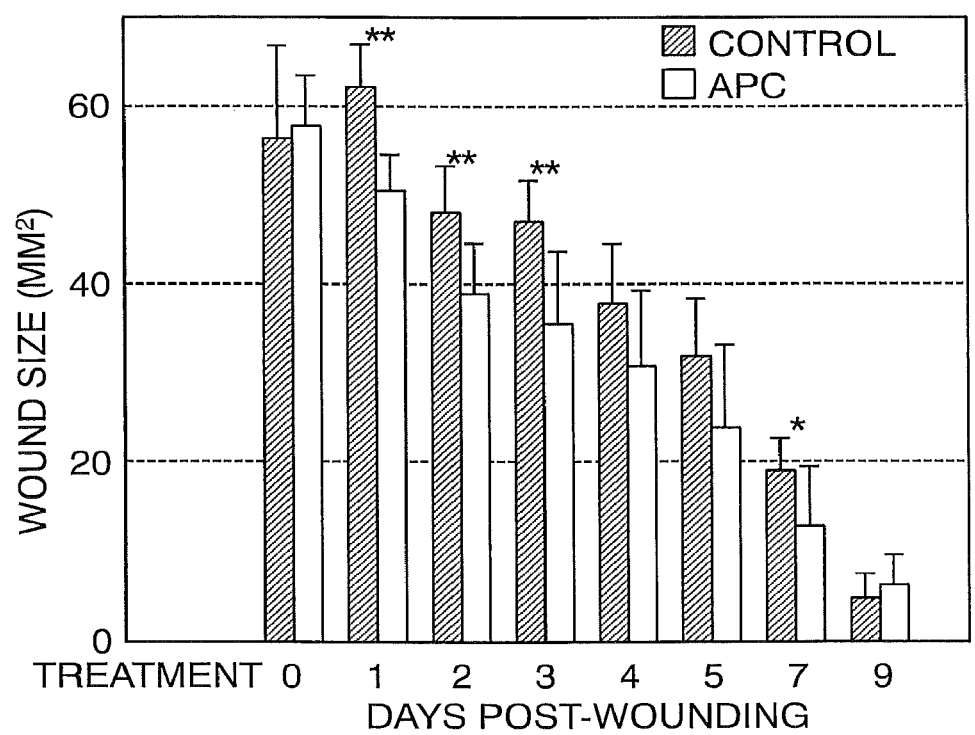
Figure 6:
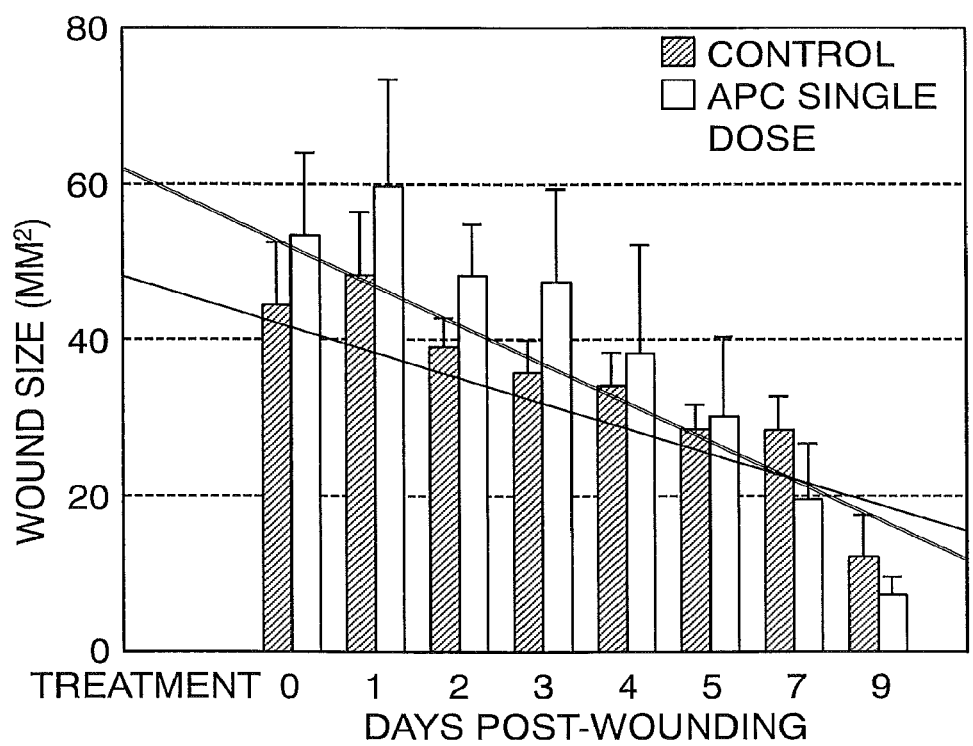

FIG. 5 shows the effect of APC on a rat wound healing model. Normal rats were wounded using an 8 mm punch biopsy and not treated (Control, 2 rats, 7 wounds) or treated twice with APC (40 μg APC immediately after wounding followed by a second treatment of 40 μg APC after 1 day) (3 rats, 11 wounds). Wound size was measured by image analysis and results shown are mean+/−S.D of wound area (mm$^2$) after 1, 2, 3, 4, 5, 7 and 9 days FIG. 6 shows the effect of APC on a diabetic rat wound healing model. Streptozotocin-induced diabetic rats were wounded using an 8 mm punch biopsy and immediately treated with 20 μg APC (2 rats, 7 wounds) or no test agent (Control, 1 rat, 4 wounds). Wound closure was assessed visually and after 1, 2, 3, 4, 5, 7 and 9 days. There was a significant difference in the rate of wound healing (slope of the regression lines) between the control and APC-treated rats, with the latter healing faster ($p<0.01$).

EXAMPLE 1

APC Promotion of Endothelial Wound Repair

Activated protein C (APC) was tested for its ability to promote repair of endothelial wounding using a modification of an in vitro assay, as described previously (19). Briefly, confluent microvascular endothelial cells (FSE) from neonatal foreskins were cultured for 5 days in 24-well culture plates in growth medium (Biorich plus 50 μg/ml heparin, 50 μg/ml endothelial cell growth supplement and 5% human serum). The endothelial monolayers were wounded by a single stroke across the diameter of the well with a pipette tip. The media and dislodged cells were then aspirated, and the plates rinsed with Hanks buffer. Fresh growth medium was added to the plates along with APC at various concentrations or the potent tumour-promoting angiogenic factor, phorbol myristate acetate (PMA) (10 ng/ml) and the cells were incubated at 37 degrees C. After 24 hr, the width of the wound was visualised microscopically and results at different doses of APC were quantified using image analysis and a dose-response curve was generated (FIG. 1). Cells cultured in the presence of 75 nM APC achieved almost complete wound closure within 24 hours, and showed more than twice the migratory response than did cells without APC. At 100 nM there was no further increase. APC (75 nM) had approximately the same activity as PMA.

EXAMPLE 2

APC Promotion of Angiogenesis

In view of the ability of APC to activate gelatinase A and promote endothelial wounding, APC was investigated as to whether it could promote angiogenesis. APC was added to the chicken embryo chorio-allantoic membrane (CAM) assay using gelatin sponges (Gelfoam). Sponges were cut to approximately 2 mm×2 mm. Five μg APC in phosphate buffered saline (PBS) or PBS alone was added to gelatin sponges which were subsequently placed on the 9 day old CAM, as previously described (34). The CAMs were inspected daily and on day 14 were photographed and fixed for histological sectioning. Macroscopically, on day 14, the APC-treated gelatin sponges were surrounded by blood vessels that grew radially inwards towards the sponge in a "spoke-wheel" pattern (data not shown). In contrast, gelatin sponges treated with PBS had no surrounding vascular formation. Histological sections showed that APC-treated sponges were infiltrated with many new blood vessels (angiogenesis) (FIG. 2). In addition, there was a large migration of fibroblasts into the APC-treated sponges. There was also marked proliferation of the epithelial layer, with the ectoderm completely growing over the gelatin sponge. Associated with this re-epithelialisation was stratification and involution at the periphery of the sponge. The endoderm also demonstrated stratification with villous formation in some sections and the presence of cells being shed from the villi (not shown). In contrast to the APC-treated sponges, there was little evidence of any re-epithelialisation, endothelial cell or fibroblast infiltration in the PBS control sponges.

EXAMPLE 3

APC Promotion of Wound Healing

In view of APC's ability to stimulate endothelial migration and enhance re-epithelialisation, fibroblast invasion and angiogenesis, APC was examined for a capacity to improve wound healing in a rat model. Sprague-Dawley rats were anaesthetised and four full-thickness wounds were excised, using a 8 mm punch biopsy, on the back of the rat, exposing the underlying dorsolateral skeletal muscle fascia. Hemostasis was achieved by even compression with sterile gauze. APC was diluted in isotonic, sterile, pyrogen-free saline solution and each excision was treated with a 50 μl topical application of sterile, pyrogen-free saline solution or saline containing 20 μg APC. The wounds were left open with no dressing and rats caged one per cage. Wound closure was assessed visually and after 40 hr, 4 days and 7 days. At each timepoint, the wounds were digitally photographed using a Nikon Coolpix 950, with a distance calibration scale in the frame. The area of the wound was calculated by image analysis (Scion Image). After 40 hr there was a marked visual improvement in the wound closure in APC-treated wounds compared to controls. On day 4 image analysis results revealed a significant reduction in wound size of APC-treated wounds compared to controls (FIG. 3). This difference was maintained on day 7 (FIG. 3c, p<0.01, *p<0.001).

EXAMPLE 4

APC Promotion of Wound Healing

APC was further examined for a capacity to improve wound healing in a rat model. Sprague-Dawley rats were anaesthetised and four full-thickness wounds were excised, using a 8 mm punch biopsy, on the back of the rat, exposing the underlying dorsolateral skeletal muscle fascia. Hemostasis was achieved by even compression with sterile gauze. APC was diluted in isotonic, sterile, pyrogen-free saline solution and each excision was immediately treated with a 50 μl topical application of sterile, pyrogen-free saline solution or saline containing the following: 0 μg APC (Control, 3 rats, 12 wounds), 10 μg APC (3 rats, 12 wounds), 40 μg APC (4 rats, 16 wounds), 70 μg APC (3 rats, 12 wounds) or 100 μg APC (3 rats, 12 wounds). The wounds were left open with no dressing and rats caged one per cage. Wound size was measured by image analysis after 1, 3, 5, 7 and 9 days. At each timepoint, the wounds were digitally photographed using a Nikon Coolpix 995. The area of the wound was calculated by image analysis (Scion Image). Results are shown in FIG. 4. After 1 day, there was a significant reduction in the size of the wounds treated with 10 or 40 μg APC. There was no difference between the controls and rats treated with 70 or 100 μg APC. The significant reduction in wound size was most notable with 40 μg APC and seen on days 1, 3, 7 and 9. (** p<0.01, * p<0.05, Student's t-test, using CoStat).

EXAMPLE 5

APC Promotion of Wound Healing

APC was further examined for a capacity to improve wound healing in a rat model. Sprague-Dawley rats were wounded as described in Example 4. APC was diluted in isotonic, sterile, pyrogen-free saline solution and each excision was treated with a 50 μl topical application of sterile, pyrogen-free saline solution or saline containing 40 μg APC. After 48 hr, wounds were treated with a second application of 40 μg APC. The wounds were left open with no dressing and rats caged one per cage. Wound closure was assessed visually and after 1, 2, 3, 4, 5, 7 and 9 days. At each timepoint, the wounds were digitally photographed using a Nikon Coolpix 995. The area of the wound was calculated by image analysis (Scion Image). Results are shown in FIG. 5. There was a significant difference in the size of the wounds after 1 day, with APC-treated rats healing faster than controls (p<0.01). This difference was also observed at days 2, 3 and 7 (** p<0.01, * p<0.05, Student's t-test, using CoStat).

EXAMPLE 6

APC Promotion of Wound Healing in Diabetic Rats

APC was examined for a capacity to improve wound healing in a diabetic rat model. The diabetic model was selected because it is a well-described model for slow wound healing (35). Diabetes was induced in Sprague-Dawley rats using the standard procedure of an IP injection of streptozotocin. After 1 week, the blood glucose levels of the rats were >20 mM, indicative of diabetes. Diabetic rats were wounded using an 8 mm punch biopsy, as described above in Example 4, and immediately treated with 20 μg APC (2 rats, 7 wounds) or no test agent (Control, 1 rat, 4 wounds). The wounds were left open with no dressing and rats caged one per cage. Wound closure was assessed visually and after 1, 2, 3, 4, 5, 7 and 9 days. At each timepoint, the wounds were digitally photographed using a Nikon Coolpix 995. The area of the wound was calculated by image analysis (Scion Image). Results are shown in FIG. 6. There was a significant difference in the rate of wound healing (slope of the regression lines) between the control and APC-treated rats, with the latter healing faster (p<0.01).

CONCLUSION

The ability of APC to repair endothelial wounding promote re-epithelialisation, fibroblast infiltration and angiogenesis, as well as accelerate wound healing in the rat, indicates that it will be an effective wound healing agent.

REFERENCES

1. Bello, Y. M. and T. J. Phillips. 2000. Recent advances in wound healing. *JAMA* 283:716-718.
2. Braddock, M., C. J. Campbell, and D. Zuder. 1999. Current therapies for wound healing: electrical stimulation, biological therapeutics, and the potential for gene therapy. *Int J Dermatol* 38:808-817.
3. Hunt, T. K., H. Hopf, and Z. Hussain. 2000. Physiology of wound healing. *Adv Skin Wound Care* 13:6-11.
4. Bello, Y. M. and T. J. Phillips. 2000. Therapeutic dressings. *Adv Dermatol* 16:253-271.
5. Yager, D. R. and B. C. Nwomeh. 1999. The proteolytic environment of chronic wounds. *Wound Repair Regen* 7:433-441.
6. Trengove, N. J., M. C. Stacey, S. MacAuley, N. Bennett, J. Gibson, F. Burslem, G. Murphy, and G. Schultz. 1999. Analysis of the acute and chronic wound environments: the role of proteases and their inhibitors. *Wound Repair Regen* 7:442-452.
7. Kahari, V. M. and U. Saarialhokere. 1997. Matrix metalloproteinases in skin. *Experimental Dermatology* 6:199-213.
8. Singer, A. J. and R. A. Clark. 1999. Cutaneous wound healing. N Engl J Med 341:738-746.
9. McDaniel, D. H., K. Ash, J. Lord, J. Newman, and M. Zukowski. 1998. Accelerated laser resurfacing wound healing using a triad of topical antioxidants. *Dermatol Surg* 24:661-664.
10. Stone, A. 1998. Hyperbaric oxygen treatment for wounds. *Plast Reconstr Surg* 101:1738-1739.
11. Brem, H., J. Balledux, T. Bloom, M.D. Kerstein, and L. Hollier. 2000. Healing of diabetic foot ulcers and pressure ulcers with human skin equivalent: a new paradigm in wound healing. *Arch Surg* 135:627-634.
12. Falanga, V. and M. Sabolinski. 1999. A bilayered living skin construct (APLIGRAF) accelerates complete closure of hard-to-heal venous ulcers. *Wound Repair Regen* 7:201-207.
13. Gillam, A. J. and C. C. Da Camara. 1993. Treatment of wounds with procuren. *Ann Pharmacother* 27:1201-1203.
14. Mazue, G., F. Bertolero, C. Jacob, P. Sarmientos, and R. Roncucci. 1991. Preclinical and clinical studies with recombinant human basic fibroblast growth factor. *Ann NY Acad Sci* 638:329-340.
15. Esmon, C. T., W. Ding, K. Yasuhiro, J. M. Gu, G. Ferrell, L. M. Regan, D. J. Stearns-Kurosawa, S. Kurosawa, T. Mather, Z. Laszik, and N. L. Esmon. 1997. The protein C pathway: new insights. *Thromb Haem* 78:70-74.
16. Boffa, M. C. and M. Karmochkine. 1998. Thrombomodulin: an overview and potential implications in vascular disorders. *Lupus* 7: Suppl, 2-5.
17. Esmon, C. T., J. M. Gu, J. Xu, D. Qu, D. J. Stearns-Kurosawa, and S. Kurosawa. 1999. Regulation and functions of the protein C anticoagulant pathway. *Haematologica* 84:363-368.
18. Baker, W. F. and B. and. 1999. Treatment of hereditary and acquired thrombophilic disorders. *Semin. Thromb. Hemostasis*. 25:387-405.
19. Morales, D. E., K. A. Mcgowan, D. S. Grant, S. Maheshwari, D. Bhartiya, M. C. Cid, H. K. Kleinman, and H. W. Schnaper. 1995. Estrogen promotes angiogenic activity in human umbilical vein endothelial cells in vitro and in a murine model. *Circulation* 91:755-763.
20. Nguyen, M., J. Arkell, and C. J. Jackson. 2000. Activated protein C directly activates human endothelial gelatinase A. *J Biol Chem* 275:9095-9098.
21. Murphy, G. 1995. Matrix metalloproteinases and their inhibitors. *Acta Orthop Scand Suppl* 266:55-60.
22. Fang, J., Y. Shing, D. Wiederschain, L. Yan, C. Butterfield, G. Jackson, J. Harper, G. Tamvakopoulos, and M. A. Moses. 2000. Matrix metalloproteinase-2 is required for the switch to the angiogenic phenotype in a tumor model. *Proc Natl Acad Sci USA* 97:3884-3889.
23. Kondo, K., H. Kinoshita, H. Ishikura, T. Miyoshi, T. Hirose, Y. Matsumori, and Y. Monden. 2001. Activation of matrix metalloproteinase-2 is correlated with invasiveness in thymic epithelial tumors. *J Surg Oncol* 76:169-175.
24. Kozaci, L. D., D. J. Buttle, and A. P. Hollander. 1997. Degradation of type ii collagen, but not proteoglycan, correlates with matrix metalloproteinase activity in cartilage explant cultures. *Arthr Rheum* 40:164-174.
25. Cheung, P. Y., G. Sawicki, M. Wozniak, W. Wang, M. W. Radomski, and R. Schulz. 2000. Matrix metalloproteinase-2 contributes to ischemia-reperfusion injury in the heart. *Circulation* 101:1833-1839.
26. Fernandez-Patron, C., M. W. Radomski, and S. T. Davidge. 1999. Vascular matrix metalloproteinase-2 cleaves big endothelin-1 yielding a novel vasoconstrictor. *Circ Res* 85:906-911.
27. Sawicki, G., E. Salas, J. Murat, H. Misztalane, and M. W. Radomski. 1997. Release of gelatinase A during platelet activation mediates aggregation. *Nature* 386:616-619.
28. Kirshenbaun, K., Zuckermann, R. N., and Dill, K. A. 1999 Designing polymers that mimic biomolecules. *Curr Opin Stract Biol* 9:530-535.
29. Sidhu, S. S., Lowman, H. B., Cunningham, B. C., and Wells, J. A. 2000 Phage display for selection of novel binding peptides. *Methods Enzymol* 328:333-363.
30. Cunningham, B. C., and Wells, J. A. 1997 Minimized proteins. *Carr Opin Struct Biol* 7:457-462.
31. Drolet, D. W., Jenison, R. D., Smith, D. E., Pratt, D., and Hicke, B. J. 1999 A high throughout platform for systematic evolution of ligands by exponential enrichment (SELEX). *Comb Chem High Throughout Screen* 2:271-278.
32. Bissantz, C., Folkers, G., and Rognan, D. 2000 Protein-based virtual screening of chemical databases. 1 Evaluation of different docking/scoring combinations. *J Med Chem* 43:4759-4767.
33. Houghten, R. A, Wilson, D. B., and Pinilla, C. 2000 Drug Discovery and vaccine development using mixture-based synthetic combinatorial libraries. *Drug Discovery Today* 5:276-285.
34. Ribatti, D., A. Gualandris, M. Bastaki, A. Vacca, M. Iurlaro, L. Roncali, and M. Presta. 1997. New model for the study of angiogenesis and antiangiogenesis in the chick embryo chorioallantoic membrane: the gelatin sponge/chorioallantoic membrane assay. *J Vasc Res* 34:455-463.
35. Taniyama Y., Morishita R., Hiraoka K., Aoki M., Nakagami H., Yamasaki K., Matsumoto K., Nakamura T., Kaneda Y., and Ogihara T. 2001 Therapeutic angiogenesis induced by human hepatocyte growth factor gene in rat diabetic hind limb ischemia model: molecular mechanisms of delayed angiogenesis in diabetes. *Circulation* 104:2344-2350.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

What is claimed is:

1. A method for promoting wound healing in a subject, said method comprising topically administering to said subject an effective amount of an agent comprising an activated protein C (APC), optionally in admixture with a pharmaceutically-acceptable carrier, wherein the wound is selected from the group consisting of dermal ulcers, burns, oral wounds, bone and cartilage damage, and warfarin-related skin necrosis.

2. The method of claim 1, wherein the agent is human APC.

3. The method of claim 1, wherein the agent is administered to said subject within 1 to 10 hours of wounding.

4. The method of claim 1, wherein the wound for which wound healing is to be promoted is a dermal ulcer.

5. The method of claim 1, wherein the effective amount of the agent is in the range of 0.1 to 1000 µg per kg of body weight.

6. The method of claim 5, wherein the effective amount of the agent is in the range of 0.1 to 10 µg per kg of body weight.

7. The method of claim 1, wherein the wound for which wound healing is promoted is an epithelial wound.

8. The method of claim 1, wherein the wound for which wound healing is to be promoted is a burn.

9. The method of claim 1, wherein the wound for which wound healing is to be promoted is an oral wound.

10. The method of claim 1, wherein the wound for which wound healing is to be promoted is bone and cartilage damage.

11. The method of claim 1, wherein the wound for which wound healing is to be promoted is a warfarin-related skin necrosis.

* * * * *